United States Patent
Talbott

(10) Patent No.: US 12,090,188 B2
(45) Date of Patent: Sep. 17, 2024

(54) NUTRITIONAL SUPPLEMENTS AFFECTING GUT-BRAIN-AXIS BALANCE AND MENTAL WELLNESS

(71) Applicant: Shawn Talbott, Draper, UT (US)

(72) Inventor: Shawn Talbott, Draper, UT (US)

(73) Assignee: AMARE GLOBAL, Irvine, CA (US)

(*) Notice: Subject to any disclaimer, the term of this patent is extended or adjusted under 35 U.S.C. 154(b) by 359 days.

(21) Appl. No.: 16/642,860

(22) PCT Filed: Aug. 30, 2018

(86) PCT No.: PCT/US2018/048980
§ 371 (c)(1),
(2) Date: Feb. 27, 2020

(87) PCT Pub. No.: WO2019/046660
PCT Pub. Date: Mar. 7, 2019

(65) Prior Publication Data
US 2021/0069280 A1   Mar. 11, 2021

Related U.S. Application Data

(60) Provisional application No. 62/552,194, filed on Aug. 30, 2017.

(51) Int. Cl.
| | |
|---|---|
| A61K 36/00 | (2006.01) |
| A23L 33/00 | (2016.01) |
| A23L 33/105 | (2016.01) |
| A61K 35/745 | (2015.01) |
| A61K 35/747 | (2015.01) |
| A61K 36/15 | (2006.01) |
| A61K 36/185 | (2006.01) |
| A61K 36/53 | (2006.01) |
| A61K 36/537 | (2006.01) |
| A61K 36/61 | (2006.01) |
| A61K 36/73 | (2006.01) |
| A61K 36/87 | (2006.01) |
| A61K 47/36 | (2006.01) |
| A61K 47/46 | (2006.01) |
| A61P 25/24 | (2006.01) |

(52) U.S. Cl.
CPC ............ *A61K 36/87* (2013.01); *A23L 33/105* (2016.08); *A23L 33/40* (2016.08); *A61K 35/745* (2013.01); *A61K 35/747* (2013.01); *A61K 36/15* (2013.01); *A61K 36/185* (2013.01); *A61K 36/53* (2013.01); *A61K 36/537* (2013.01); *A61K 36/61* (2013.01); *A61K 36/73* (2013.01); *A61K 47/36* (2013.01); *A61K 47/46* (2013.01); *A61P 25/24* (2018.01); *A23V 2002/00* (2013.01)

(58) Field of Classification Search
None
See application file for complete search history.

(56) References Cited

U.S. PATENT DOCUMENTS

| | | |
|---|---|---|
| 7,781,572 B2 | 8/2010 | Bartlett et al. |
| 7,794,761 B2 | 9/2010 | Shelby et al. |
| 9,028,890 B2 * | 5/2015 | Ferrari .................. A61P 43/00 424/725 |
| 9,700,071 B2 | 7/2017 | Silver et al. |
| 10,213,471 B1 | 2/2019 | Buckner |
| 10,449,148 B2 | 10/2019 | Gutierrez et al. |
| 2003/0206972 A1 | 11/2003 | Babish et al. |
| 2007/0269541 A1 | 11/2007 | Rohdewald |
| 2009/0148433 A1 | 6/2009 | Naidu et al. |
| 2011/0206649 A1 | 8/2011 | Bergonzelli et al. |
| 2011/0262618 A1 | 10/2011 | Melwitz |
| 2013/0064803 A1 | 3/2013 | Naidu et al. |
| 2013/0164394 A1 | 6/2013 | Ferrari et al. |
| 2013/0261183 A1 | 10/2013 | Bhagat |
| 2014/0037603 A1 | 2/2014 | Bolster et al. |
| 2016/0000854 A1 | 1/2016 | Osborne et al. |
| 2019/0183849 A1 | 6/2019 | Kariman |
| 2020/0297605 A1 | 9/2020 | Ambrogio et al. |
| 2020/0352206 A1 | 11/2020 | Wagner-Salvini |
| 2020/0397711 A1 | 12/2020 | Lee |
| 2021/0038656 A1 | 2/2021 | Tripp et al. |
| 2021/0121490 A1 | 4/2021 | Takahashi et al. |

FOREIGN PATENT DOCUMENTS

| | | |
|---|---|---|
| CN | 106615516 A | 5/2017 |
| CN | 110179121 A | 8/2019 |
| WO | 03/21515 A2 | 3/2003 |
| WO | 2014083438 A2 | 6/2014 |
| WO | 2015/006646 A1 | 1/2015 |
| WO | 2015/153841 A1 | 10/2015 |

(Continued)

OTHER PUBLICATIONS

Ku et al. (2008) Wood Sci. Technol. 42; 47-60. (Year: 2008).*
Frotela-Saseta et al. (2011) Phytother. Res. 25: 1870-1875. (Year: 2011).*
Lizarraga et al. (2007) FEBS Journal 274: 4802-4811. (Year: 2007).*
McGann et al. (2007) Food and Chemical Toxicology 45: 1224-1230. (Year: 2007).*
Radhakrishnan et al. (2011) Frontiers in Bioscience E3, 1509-1523. (Year: 2011).*
Reagan-Shaw et al. (2010) Nutrition and Cancer 62(4): 517-524. (Year: 2010).*

(Continued)

*Primary Examiner* — Russell G Fiebig
(74) *Attorney, Agent, or Firm* — HOLLAND & HART LLP

(57) ABSTRACT

Nutritional supplement compositions are disclosed for improving health and function of the gut-brain-axis (GBX) and one or more mood states (MS) of an individual—also described as Mental Wellness (MW). Nutritional supplements disclosed herein may include plant material from any combination of (1) pine bark, (2) grape seed, and (3) apple fruit and peel. Related processes are also disclosed.

4 Claims, 2 Drawing Sheets

(56) References Cited

FOREIGN PATENT DOCUMENTS

| WO | 2018/013871 A1 | 1/2018 |
| WO | 2018/027070 A1 | 2/2018 |
| WO | 2018/035212 A1 | 2/2018 |
| WO | 2018/195097 A1 | 10/2018 |
| WO | 2019/056129 A2 | 3/2019 |
| WO | 2019/069096 A1 | 4/2019 |
| WO | 2019/078005 A1 | 4/2019 |
| WO | 2019/090273 A2 | 5/2019 |

OTHER PUBLICATIONS

Rohdewald (2002) Intern. J. Clin. Pharmacol. Ther. vol. 40, No. 4: (158-168). (Year: 2002).*
Veeriah et al. (2006) Molecular Carcinogenesis 45:164-174. (Year: 2006).*
Kaur et al. (2008) Nutr. Cancer 60(Suppl. 1): 2-11. (Year: 2008).*
Raskin et al. (2004) Current Pharmaceutical Design 10: 3419-3429. (Year: 2004).*
Revilla et al. (1998) J. Agric. Food Chem. 46: 4592-4597. (Year: 1998).*
"International Search Report and Written Opinion of the International Searching Authority," issued in connection with Int'l Appl. No. PCT/US18/48945, dated Nov. 21, 2018 (7 pages).
"International Search Report and Written Opinion of the International Searching Authority," issued in connection with Int'l Appl. No. PCT/US18/48980, dated Nov. 30, 2018 (7 pages).
"International Search Report and Written Opinion of the International Searching Authority," issued in connection with Int'l Appl. No. PCT/US20/49469 dated Dec. 10, 2020 (8 pages).
"International Search Report and Written Opinion of the International Searching Authority," issued in connection with Int'l Appl. No. PCT/US20/49545, dated Dec. 10, 2020 (14 pages).
"International Search Report and Written Opinion of the International Searching Authority," issued in connection with Int'l Appl. No. PCT/US20/49555, dated Dec. 21, 2020 (13 pages).
"International Search Report and Written Opinion of the International Searching Authority," issued in connection with Int'l Appl. No. PCT/US20/49560, dated Jan. 7, 2021 (8 pages).
Amare Global, product names Sleep+, p. 2, Key Ingredients, Clinical Study at 2013, https://www.amare.com/corporate/SleepPlus, 1 page; retrieved Feb. 21, 2020.
Ambati, R. et al. Astaxanthin: Sources, Extraction, Stability, Biological Activities and its Commercial Applications—A Review. Marine Drugs 12:128-152, 2014. (Year: 2014).
Ji, X. et al. Astaxanthin Improves Cognitive Performance in Mice . . . Brain Research 1659:88-95, 2017. (Year: 2017).
Jiang, T. Health Benefits of Culinary Herbs and Spices J of AOAC Int 102(2)395-411 Mar./Apr. 2019. (Year: 2019).
Kapoor et al. (2009) J. Agric. Food Chem. 57: 5358-5364. (Year: 2009).
Kiralan et al. (2014) Industrial Crops and Products 57: 52-58. (Year: 2014).
Lotterodt et al. (2010) LWT-Food Science and Technology 43: 1409-1413. (Year: 2010).
Nature's Plus, Ageless Mood Support, title, p. 1, Supplement Facts, Apr. 27, 2015, https://www.amazaon.com/Natrues-Plus-Ageloss-Mood-Support/dp/B00CELG1XI; r1 page, retrieved Feb. 21, 2020.
Schauss A. Advances in the Study of the Health Benefits and Mechanisms of Action of the Pulp and Seed of the Amazonian Palm Fruit, Euterpe oleracea Mart. Known as Acai. Chapter 10 of Fruits, Vegetables and Herbs, 2016. (Year: 2016).
Sorndech, W. et al. Isomalto-Oligosaccharides: Recent Insights in Production Technology and Their Use for Food and Medical Applications. Food Science and Technology 95:135-142, 2018. (Year: 2018).
Speranza et al., "Astaxanthin Treatment Reduced Oxidative Induced Pro-Inflammatory Cytokines Secretion in U937: SHP-1 as a Novel Biological Target", Marine Drugs, vol. 20, Issue 4, Apr. 2012, pp. 890-899.
Sreedhar A. et al. Next-Gen Therapeutics for Skin Cancer: Nutraceuticals Nutrition and Cancer 70(5)697-709 Jul. 2019. (Year: 2019).
Talbott et al. "Effect of coordinated probiotic/prebiotic/phytobiotic supplementation on microbiome balance and psychological mood state in healthy stressed adults" Functional Foods in Health and Disease, Apr. 30, 2019; 9(4):265-275.
Talbott, S. et al. "Effect of Monocot Grass Extract on mood state and sleep patterns in moderately stress subjects", J Int Soc Sports Nutr. 2013, 10 (Suppl 1): p. 26. (Year: 2013).
University of Wisconsin School of Medicine and Health (Non-Pharmaceutical Approaches for Depression Towards Vitality, Pearls for Clinicians, Mar. 12, 2007). (Year: 2007).
Yamashita, E. Let Astaxanthin Be Thy Medicine PharmaNutrition 3:115-122, 2015. (Year: 2015).
Kristin Schmidt, Philip J. Cowen, Catherine J. Harmer, George Tzortzis, Steven Errington, Philip W. J. Burnet, Prebiotic intake reduces the waking cortisol response and alters emotional bias in healthy volunteers, 2015, Psychopharmacology, vol. 232, pp. 1793-1801 (Year: 2015).
L.M. Foster, T.A. Tompkins and W.J. Dahl, A comprehensive post-market review of studies on a probiotic product containing Lactobacillus helveticus R0052 and Lactobacillus rhamnosus R0011, 2011, Beneficial Microbes, vol. 2, Issue 4, pp. 319-334 (Year: 2011).
Michael Messaoudi et al., Beneficial psychological effects of a probiotic formulation (Lactobacillus helveticus R0052 and Bifidobacterium longum R0175) in healthy human volunteers, 2011, Gut Microbes, vol. 2, No. 4, pp. 256-261 (Year: 2011).
Mexican Patent Application No. MX/a/2020/002314, Substantive Examination Report dated Jul. 28, 2023; 9 pages.
Vulevic et al. (2008), "Modulation of the fecal microflora profile and immune function by a novel trans-galactooligosaccharide mixture (B-GOS) in healthy elderly volunteers," Am J Clin Nutr 2008;88: 1438-46.

* cited by examiner

Mood State Sub-Scales

NUTRITIONAL SUPPLEMENTS AFFECTING GUT-BRAIN-AXIS BALANCE AND MENTAL WELLNESS

CROSS REFERENCE TO RELATED APPLICATIONS

This application is a U.S. National Stage Entry and claims priority to PCT International Patent Application No. PCT/US2018/048980, filed Aug. 30, 2018, and entitled "NUTRITIONAL SUPPLEMENTS AFFECTING GUT-BRAIN-AXIS BALANCE AND MENTAL WELLNESS", which claims priority to U.S. Provisional Patent Application No. 62/552,194 filed Aug. 30, 2017, the entire disclosures of which are incorporated herein by this reference.

TECHNICAL FIELD

The present disclosure relates generally to the field of nutritional treatments and supplements. More particularly, the present disclosure relates to nutritional treatments and supplements for, among other things, improving health and function of the gut-brain-axis (GBX) and one or more mood states (MS) of an individual, also described as Mental Wellness (MW).

BACKGROUND OF THE INVENTION

Nutritional supplements are routinely used to improve health and/or physical performance. While nutritional supplements may be tailored to provide specific health and/or performance benefits, relatively few supplements provide such benefits while simultaneously improving GBX function and MS/MW.

DETAILED DESCRIPTION

Figure 1:
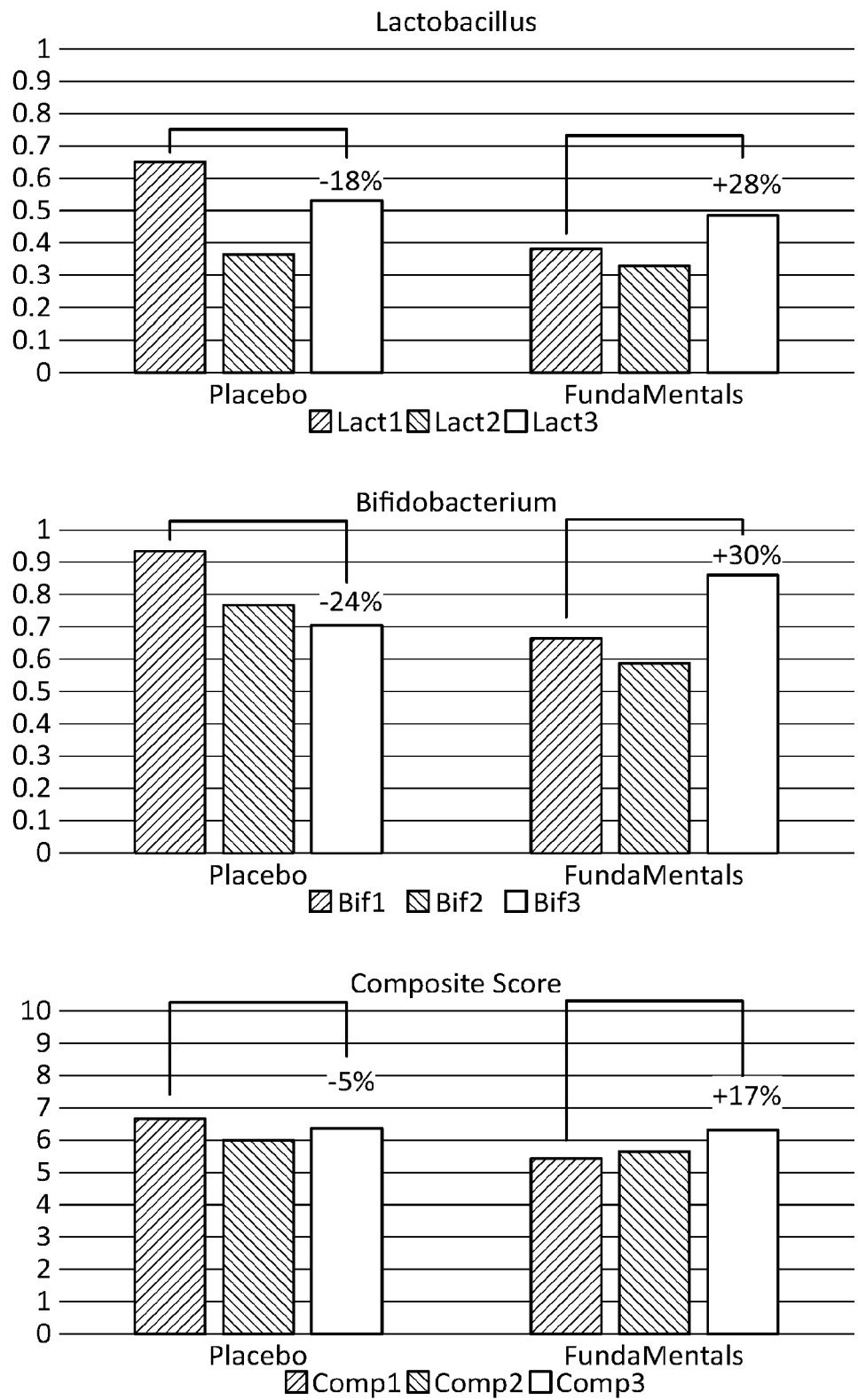
FIG. 1 illustrates the results of 30 days of supplementation, there was a significant increase in populations of "good" bacteria in the Supplement group (+28% *Lactobacillus*; +30% *Bifidobacterium*) and overall composite score† (+17% versus Placebo (p<0.05). The composite score is an overall average of many different aspects of microbiome balance, including *Bifidobacterium, Lactobacillus, Akkermansia, Firmicutes/Bacteroidetes* (F/B) ratio, and others.

The present disclosure relates to nutritional treatments and supplements, and more particularly, to nutritional treatments and/or supplements that improve GBX function and MS/MW of an individual. The following detailed description of various embodiments is not intended to limit the scope of the present disclosure, but is merely representative of various embodiments.

Amounts, concentrations, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, an amount of from 1 mg to 200 mg should be interpreted to include not only the explicitly recited limits of 1 mg and about 200 mg, but also to include individual amounts such as 2 mg, 3 mg, 4 mg, and sub-ranges such as 10 mg to 50 mg, 20 mg to 100 mg, etc. Unless otherwise stated, all ranges include both endpoints. The terms "negative mood state" and "positive mood state" are defined as described in Example 1 and elsewhere in the detailed description.

Nutritional supplements disclosed herein may include plant material from any combination of (1) pine bark, (2) grape seed, and (3) apple fruit and peel.

For example, in some embodiments, a nutritional supplement may include plant material from pine bark of the species *Pinus radiata* (commonly referred to as New Zealand pine). In some embodiments, the plant material is extracted from the pine bark. More particularly, in some instances, the plant material is extracted by using water as the primary (or exclusive) solvent. In some instances, the nutritional supplement includes between about 10 and about 100 mg, between about 10 and about 75 mg; between about 10 and about 50 mg; between about 10 and about 25 mg; between about 25 and about 100 mg; between about 25 and about 75 mg; between about 25 and about 50 mg; or between about 35 and about 65 mg of pine bark extract. In some embodiments, the pine bark extract, if dried, is between approximately 70-95% proanthocyanidin by weight. In some embodiments, plant material from the species of the genus *Pinus* is between 1% and 33% of the nutritional supplement by weight.

In some embodiments, the species of the grape seed from which plant material is derived may be *Vitus vinifera, Vitus amurensis*, or *Vitus lambrusca*. More particularly, in some embodiments, the species of the genus *Vitus* from which plant material is derived, when dried, has a total proanthocyanidin content of about 95% with about 5% content of catechin and about 15% content of epicatechin by weight. In some embodiments, the nutritional supplement includes between about 5 mg and about 200 mg, between about 25 mg and about 200 mg; between about 70 mg and about 200 mg; between about 100 mg and about 200 mg; between about 150 mg and about 200 mg; between about 15 mg and about 150 mg; between about 15 mg and about 100 mg; between about 15 mg and about 50 mg, between about 40 mg and about 130 mg; or between about 40 mg and about 75 mg of plant material from a species of the genus *Vitus*. In some embodiments, plant material from the species of the genus *Vitus* is between about 1% and about 33% of the nutritional supplement by weight.

In some embodiments, the species of the Apple fruit/peel from which plant material is derived may be *Malus domestica* or *Malus pumila*. More particularly, in some embodiments, the species of *Malus* from which plant material is derived, when dried, has a total polyphenol content of about 50% by weight. In some embodiments, the nutritional supplement includes between about 5 mg and about 200 mg, between about 25 mg and about 200 mg; between about 70 mg and about 200 mg; between about 100 mg and about 200 mg; between about 150 mg and about 200 mg; between about 15 mg and about 150 mg; between about 15 mg and about 100 mg; between about 15 mg and about 50 mg, between about 40 mg and about 130 mg; or between about 40 mg and about 75 mg of plant material from a species of the genus *Malus*. In some embodiments, plant material from the species of the genus *Malus* is between about 1% and about 33% of the nutritional supplement by weight.

In addition to plant material from pine bark, plant material from apple fruit/peel, and plant material from grape seed, some nutritional supplements disclosed herein may include one or more of the following ingredients: probiotics, prebiotics, theanine, artichoke, ginger, glutamine, pomegranate, rosemary, oregano, clove, sage, holy basil, guayusa, green tea, caffeine, tyrosine, cysteine, astaxanthin, and tocotrienols.

For instance, in some embodiments, a nutritional supplement includes probiotic bacteria from species associated with mental wellness (anti-depression or anti-anxiety) such as *L. helveticus, B. longum,* or *L. rhamnosus*; and prebiotic fibers such as galacto-oligo-saccharide or galactomannan in an amount of between about 1 billion and about 10 billion colony-forming units (CFU) in the case of probiotic bacteria; and between about 1,000 mg and about 10,000 mg in the case of prebiotic fiber.

In some embodiments, the amount of theanine in a nutritional supplement may be between about 5 mg and about 150 mg. In some embodiments, the amount of artichoke in a nutritional supplement may be between about 5 mg and about 250 mg. In some embodiments, the amount of ginger may be between about 1 mg and about 50 mg. In some embodiments, the amount of glutamine in a nutritional supplement may be between about 10 mg and about 200 mg.

In some embodiments, the amount of pomegranate in a nutritional supplement may be between about 50 mg and about 500 mg. In some embodiments, the amount of rosemary in a nutritional supplement may be between about 20 mg and about 200 mg. In some embodiments, the amount of oregano may be between about 20 mg and about 200 mg. In some embodiments, the amount of clove in a nutritional supplement may be between about 10 mg and about 100 mg. In some embodiments, the amount of sage in a nutritional supplement may be between about 10 mg and about 100 mg. In some embodiments, the amount of holy basil in a nutritional supplement may be between about 10 mg and about 100 mg.

In some embodiments, the amount of guayusa in a nutritional supplement may be between about 50 mg and about 250 mg. In some embodiments, the amount of pomegranate in a nutritional supplement may be between about 50 mg and about 250 mg. In some embodiments, the amount of green tea may be between about 50 mg and about 150 mg. In some embodiments, the amount of caffeine in a nutritional supplement may be between about 1 mg and about 200 mg.

In some embodiments, the amount of tyrosine in a nutritional supplement may be between about 25 mg and about 500 mg. In some embodiments, the amount of cysteine in a nutritional supplement may be between about 25 mg and about 250 mg. In some embodiments, the amount of astaxanthin may be between about 1 mg and about 15 mg. In some embodiments, the amount of tocotrienols in a nutritional supplement may be between about 5 mg and about 100 mg.

In some embodiments, a nutritional supplement may be formulated as a capsule, tablet or softgel. For example, in some embodiments, ingredients of the nutritional supplement may be blended in various combinations described to form a single-dose delivery.

In some embodiments, a nutritional supplement may be formulated as a powdered drink mix. For example, in some embodiments, ingredients of the nutritional supplement may be mixed into a base liquid, such as water or juice to form a drinkable mixture—or may be mixed into a base food, such as oatmeal or yogurt to form an edible mixture. In some embodiments, the liquid drink may be between about 1 and about 20 ounces in weight. In some embodiments, the nutritional supplement may be combined into a food base as a functional food including snack bars and meal replacement shakes.

In some embodiments, the nutritional supplement may be effective for increasing positive mood state, as measured by self-reported feelings of energy, mood, focus, and well-being, when the nutritional supplement is administered to a healthy adult and/or a person suffering from mood disorders. For instance, in some embodiments, the nutritional supplement may increase average positive mood state—as measured on 100 mm visual analog scales (VAS)—by more than 10%, more than 25%, more than 40%, more than 60%, more than 70%, more than 80%, and/or more than 90%. Additionally or alternatively, average positive mood state may increase as a result of consumption of the nutritional supplement by more than approximately 10 VAS, 15 VAS, 20 VAS, 25 VAS, and/or 30 VAS, where each VAS unit corresponds to each mm along a 100 mm visual analog scale.

Additionally or alternatively, the nutritional supplement may, in some embodiments, be effective for decreasing negative mood state, as measured by self-reported feelings of stress, tension, irritability, and anxiety, when the nutritional supplement is administered to a healthy adult and/or a person suffering from mood disorders. In some embodiments, the nutritional supplement may decrease average negative mood state—as measured on 100 mm visual analog scales—by more than 10%, more than 15%, more than 20%, more than 30%, more than 35%, and/or more than 40%. Additionally or alternatively, average negative mood state may decrease by more than 5 VAS, 8 VAS, 10 VAS, 12 VAS, and/or 15 VAS as a result of consumption of the nutritional supplement.

In some embodiments, the nutritional supplement may decrease levels of detrimental bacteria (e.g. *Clostridium* species) and increase levels of beneficial bacteria (e.g. *Bifidobacterium* species) when administered to a healthy adult. For example, in some embodiments, the concentration of detrimental gut bacteria may decrease by at least about 5%, 10%, and/or 30%. In some embodiments, the consumption of the nutritional supplement also increases levels of beneficial bacteria by about 30%, 50% and/or 70%.

In some embodiments, the nutritional supplement may exhibit immune system benefits and anti-inflammatory benefits. Stated differently, in some embodiments, the nutritional supplement may be effective for improving immune system vigilance and communication between the gut and the brain when administered to a healthy adult. For example, in some embodiments, consumption of the nutritional supplement may cause an immune-supported reduction in gastrointestinal inflammation and neuro-inflammation as well as an increase in global mood state and overall well-being resting of more than 5%, 10%, 20%, and/or 30%.

Example 1

A first trial was completed to evaluate the effect of using a nutritional supplement combination that includes plant material from New Zealand pine (*Pinus radiata*) bark, Asian apple (*Malus domestica*) fruit/peel, and French grape (*Vitus vinifera*) seed. In the trial, thirty-two healthy subjects were screened for "moderate" levels of psychological stress and were then randomly assigned to 30-days of a supplement per the present disclosure. In this example, the supplement contained specific strains of probiotic bacteria, prebiotic fibers, and phytobiotic plant extracts, as set out in Table 1 or Table 2, N=21) or a look-alike Placebo (N=11).

TABLE 1

| Ingredient | Amount in a single serving |
| --- | --- |
| Extracts from New Zealand pine (*Pinus radiata*) bark, Asian apple (*Malus domestica*) fruit/peel, and French grape (*Vitus vinifera*) seed | 50 mg |
| Prebiotic bacteria (*L. helveticus, B. longum*, and *L. rhamnosus*) | 3 Billion CFU |
| Prebiotic fiber (galacto-oligosaccharide and galactomannan) | 3,000 mg |
| Digestive blend (glutamine, artichoke leaf, ginger root) | 160 mg |

TABLE 2

| Ingredient | Amount in a single serving |
| --- | --- |
| Extracts from New Zealand pine (*Pinus radiata*) bark, Asian apple (*Malus domestica*) fruit/peel, and French grape (*Vitus vinifera*) seed | 125 mg |
| Pomegranate extract (Wonderful variety, *Punica granatum*) whole fruit | 225 mg |
| Rosemary extract | 100 mg |
| Oregano extract | 100 mg |
| Clove extract | 50 mg |
| Sage extract | 25 mg |
| Holy basil extract | 25 mg |

The subjects in this study were "healthy stressed" individuals—meaning they represent the vast majority of the population who have stress, fatigue, brain fog, and the modern 21st century "syndrome of the blahs".

Microbiome balance was assessed in fecal samples using a PCR-based analysis (BiomeTracker) that has previously compared favorably to 16S sequencing (ACN 2017) for abundance quantification for major phyla/families of bacteria. Psychological mood state parameters were assessed using the validated Profile of Mood States survey (POMS) to generate scores for Global Mood State, and six sub-scales (Depression, Tension, Fatigue, Anger, Confusion, and Vigor).

Figure 2:
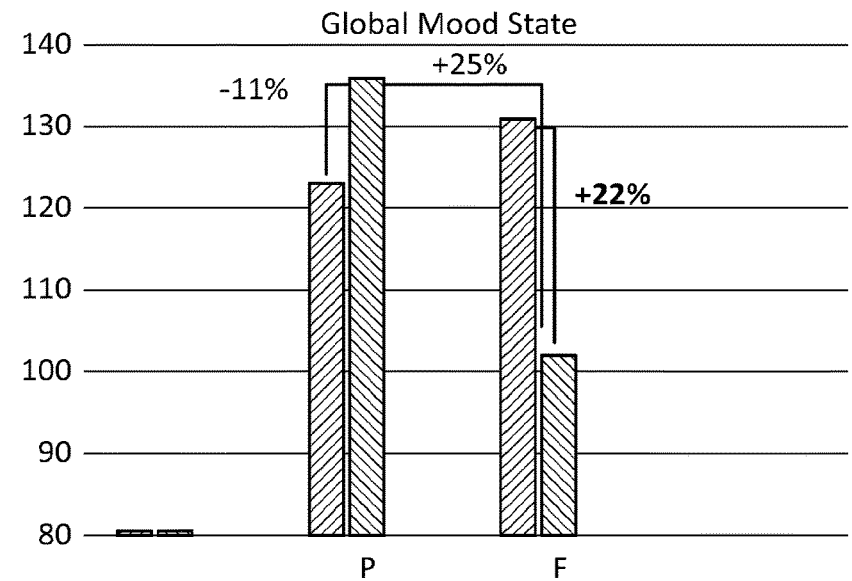
FIG. 2 shows significant improvement of psychological indices in the Supplement group for both positive (+25% Global Mood; +44% Vigor) and negative (−55% Depression; −45% Tension; −64% Fatigue; −43% Confusion; −54% Anger) mood state parameters versus Placebo (p<0.05).
Figure 2:
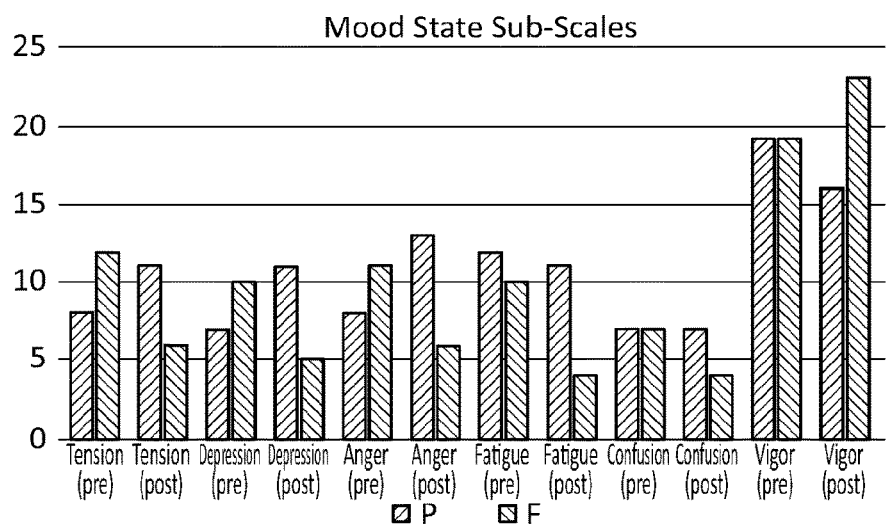
Figure 2:
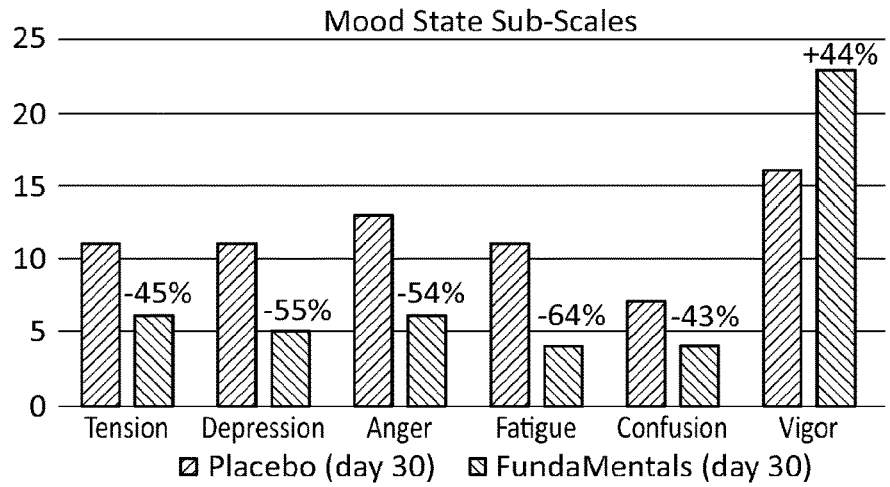

Following 30-days of supplementation, there was a significant increase in populations of "good" bacteria in the Supplement group (+28% *Lactobacillus*; +30% *Bifidobacterium*) and overall composite score (+17%) versus Placebo ($p<0.05$) (see FIG. 1). The composite score is an overall average of many different aspects of microbiome balance, including *Bifidobacterium, Lactobacillus, Akkermansia, Firmicutes/Bacteroidetes* (F/B) ratio, and others. Psychological indices were significantly improved in the Supplement group for both positive (+25% Global Mood; +44% Vigor) and negative (−55% Depression; −45% Tension; −64% Fatigue; −43% Confusion; −54% Anger) mood state parameters versus Placebo ($p<0.05$) (see FIG. 2).

Example 2

A series of studies will be conducted to evaluate the effect of using a nutritional supplement combination that includes plant material from New Zealand pine (*Pinus radiata*) bark, Asian apple (*Malus domestica*) fruit/peel, and French grape (*Vitus vinifera*) seed. More particularly, a multi-component nutritional supplement system that includes the ingredients set forth in Tables 3-6 will be delivered orally to healthy adults. The amount of each listed ingredient in the nutritional supplement system is also set forth in the same table.

TABLE 3

| Ingredient | Amount in a single serving |
| --- | --- |
| Extracts from New Zealand pine (*Pinus radiata*) bark, Asian apple (*Malus domestica*) fruit/peel, and French grape (*Vitus vinifera*) seed | 50 mg |
| Prebiotic bacteria (*L. helveticus, B. longum*, and *L. rhamnosus*) | 3 Billion CFU |
| Prebiotic fiber (galacto-oligosaccharide and galactomannan) | 3,000 mg |
| Digestive blend (glutamine, artichoke leaf, ginger root) | 160 mg |

TABLE 4

| Ingredient | Amount in a single serving |
| --- | --- |
| Extracts from New Zealand pine (*Pinus radiata*) bark, Asian apple (*Malus domestica*) fruit/peel, and French grape (*Vitus vinifera*) seed | 125 mg |
| Pomegranate extract (Wonderful variety, *Punica granatum*) whole fruit | 225 mg |
| Rosemary extract | 100 mg |
| Oregano extract | 100 mg |
| Clove extract | 50 mg |
| Sage extract | 25 mg |
| Holy basil extract | 25 mg |

TABLE 5

| Ingredient | Amount in a single serving |
| --- | --- |
| Extracts from New Zealand pine (*Pinus radiata*) bark, Asian apple (*Malus domestica*) fruit/peel, and French grape (*Vitus vinifera*) seed | 75 mg |
| Guayusa leaf extract | 100 mg |
| Pomegranate fruit extract | 100 mg |
| Natural caffeine | 55 mg |

TABLE 6

| Ingredient | Amount in a single serving |
| --- | --- |
| Extracts from New Zealand pine (*Pinus radiata*) bark, Asian apple (*Malus domestica*) fruit/peel, and French grape (*Vitus vinifera*) seed | 90 mg |
| L-Tyrosine | 125 mg |
| N-acetyl-L-cysteine | 62.5 mg |
| Tocotrienols | 5 mg |
| Astaxanthin | 1 mg |

Twenty healthy active adult subjects will be recruited to participate in a 4-week supplementation study.

Before and after the supplementation period, the mood state of each subject will be analyzed through the use of 100 mm visual analog scales. More specifically, negative mood state will be assessed by asking each participant to mark 100 mm visual analog scales in a manner that reflects their subjective perception of mood state parameters relating to negative mood state (i.e., stress, tension, irritability, anxiety)

and positive mood state (i.e., energy, mood, focus, well-being). A mark on the far left side of the visual analog scale (corresponding to 0 VAS) means that the specified parameter is not noticeable, while a mark on the far right side of the scale (corresponding to 100 VAS) means that the subject perceives the maximal amount with respect to that parameter. The scores from the four mood state parameters for negative mood state will be averaged to determine the negative mood state at each time point. Scoring for the positive mood state will be calculated in an analogous manner.

Expected Results

Based on previous pilot studies, the subjects are expected to report an overall improvement of mood state with the nutritional supplement intervention relative to the control intervention. More particularly, the average post-consumption negative mood state for the supplement intervention will be decreased relative to the average negative mood state reported by subjects for the control intervention (~30-40 VAS). Conversely, the average post-supplementation positive mood state will be significantly increased (~20-40 VAS) relative to the average positive mood state reported by subjects for the control intervention. Without being limited to any particular theory, it is believed that the combination of both (1) increased positive mood state and (2) decreased negative mood state that is elicited by the nutritional supplement of Example 1 is a characteristic that is markedly different from any naturally occurring counterpart(s) of the nutritional supplement in their natural state.

In short, different levels of servings of the nutritional supplement described in this example unexpectedly produced both a decrease in negative mood state and an increase in positive mood state.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

This disclosure should not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

It will be apparent to those having skill in the art that changes may be made to the details of the above-described embodiments without departing from the underlying principles of the present disclosure.

What is claimed is:

1. A method of altering the mood state of a human subject, comprising administering to the human subject an effective amount of a nutritional supplement comprising:
   between about 10 mg and about 100 mg of pine bark extract from the species *Pinus radiata*;
   between about 10 mg and about 100 mg of apple fruit extract from apple peel from the species *Malus domestica*;
   between about 10 mg and about 100 mg of grape seed extract from the species *Vitus vinifera*;
   between about 1 billion and about 10 billion colony-forming units of *L. helveticus*;
   between about 1 billion and about 10 billion colony-forming units of *B. longum*;
   between about 1 billion and about 10 billion colony-forming units of *L. rhamnosus*;
   between about 1,000 mg and about 10,000 mg of galacto-oligosaccharide;
   between about 1,000 mg and about 10,000 mg of galactomannan;
   between about 10 mg and about 200 mg of glutamine;
   between about 5 mg and about 250 mg of artichoke leaf extract; and
   between about 1 mg and about 50 mg of ginger root extract,
   wherein the effective amount is effective to modulate fecal bacteria in the human subject.

2. The method of claim 1, wherein the method increases positive mood state in the human subject.

3. The method of claim 1, wherein the method decreases negative mood state in the human subject.

4. The method of claim 1, wherein the method improves sleep quality in the human subject.

* * * * *